United States Patent [19]
Batt et al.

[11] Patent Number: 5,545,523
[45] Date of Patent: Aug. 13, 1996

[54] METHODS OF DETECTING BOVINE HERPESVIRUS 1 (BHV-1) IN SEMEN BY NUCLEIC ACID AMPLIFICATION

[75] Inventors: Carl Batt, Groton; Martin Wiedmann, Ithaca; Richard Brandon, Dryden, all of N.Y.

[73] Assignee: Cornell Research Foundation, Inc., Ithaca, N.Y.

[21] Appl. No.: 70,156

[22] Filed: May 28, 1993

[51] Int. Cl.$^6$ .............................. C12Q 1/68; C12Q 1/70; C12P 19/34
[52] U.S. Cl. .................... 435/6; 435/5; 435/91.1; 536/23.1; 536/24.3; 536/24.32; 536/24.33; 935/77; 935/78
[58] Field of Search .................... 435/6, 91.1, 5; 536/23.1, 24.3, 24.32, 24.33; 935/77, 78

[56] References Cited

U.S. PATENT DOCUMENTS

| | | | |
|---|---|---|---|
| 4,824,667 | 4/1989 | Kit et al. | 424/89 |
| 5,087,693 | 2/1992 | Levings et al. | 530/387 |
| 5,128,129 | 7/1992 | Kit et al. | 424/89 |
| 5,151,267 | 9/1992 | Babiuk et al. | 424/89 |

OTHER PUBLICATIONS

Chase et al. J. Virology 64(10):4866–4872, 1990.
Fehler et al. J. Virology 66(2):831–839, 1992.
Tikoo et al., "Molecular Cloning, Sequencing and Expression of Functional Bovine Herpesvirus 1 Glycoprotein gIV in Transfected Bovine Cells", Journal of Virology, Vol. 64, No. 10, Oct., 1990, pp. 5132–5142.

Israel et al., "Induction of a Mucosal Barrier to Bovine Herpesvirus 1 Replication in Cattle", Virology, Vol. 188, pp. 256–264 (1992).

Vilcek, "Detection of the bovine herpesvirus–1 (BHV–1) genome by PCR", Journal of Virological Methods, Vol. 41, (1993), pp. 245–248.

*Primary Examiner*—W. Gary Jones
*Assistant Examiner*—Paul B. Tran
*Attorney, Agent, or Firm*—Hodgson, Russ, Andrews, Woods & Goodyear

[57] ABSTRACT

The present invention relates to novel compositions comprising Bovine Herpesvirus-1 (BHV-1) specific oligonucleotides which are useful as nested primers to amplify sequences of the BHV-1 gIV gene during enzymatic nucleic acid amplification. The invention also provides a method for the detection of BHV-1 which may be present in a clinical specimen, particularly bovine semen, using the BHV-1 specific nested primers and enzymatic nucleic acid amplification. The present invention also relates to a BHV-1 specific oligonucleotide which can be used as a probe to facilitate detection of amplified products derived from BHV-1 gIV gene sequences.

8 Claims, 3 Drawing Sheets

```
First Stage:
5'
   GCTGTGGGAAGCGGTACG→ extends
   ||||||||||||||||||
---CGACACCCTTCGCCATGC---TGCCAGTATACCATGTTCTAGCTCTCGC--
---GCTGTGGGAAGCGGTACG---ACGGTCATATGGTACAAGATCGAGAGCG--

-CGAAGGACCGCCCGAAGCGGATGG---CCGAGCGCCCATGTGGAAACC---CGTGTGTTCCGGTATCAGCTG---
-GCTTCCTGGCCGGGCTTCGCCTACC---GGCTCGCGGGTACACCTTTGG---GCACACAAGGCCATAGTCGAC---
                                                    ||||||||||||||||||||
                                          extends ←CGTGTGTTCCGGTATCAGCTG
                                                                       5'
                        ↓
CGACACCCTTCGCCATGC---TGCCAGTATACCATGTTCTAGCTCTCGC---CGAAGGACCGCCCGAAGCGGATGG--
GCTGTGGGAAGCGGTACG---ACGGTCATATGGTACAAGATCGAGAGCG---GCTTCCTGGCGGGCTTCGCCTACC--

-CCGAGCGCCCATGTGGAAACC---CGTGTGTTCCGGTATCAGCTG
-GGCTCGCGGGTACACCTTTGG---GCACACAAGGCCATAGTCGAC

Second Stage:
              5'     ACGGTCATATGGTACAAGATCGAGAGCG→ extends
                     ||||||||||||||||||||||||||||
CGACACCCTTCGCCATGC---TGCCAGTATACCATGTTCTAGCTCTCGC---CGAAGGACCGCCCGAAGCGGATGG--
GCTGTGGGAAGCGGTACG---ACGGTCATATGGTACAAGATCGAGAGCG---GCTTCCTGGCGGGCTTCGCCTACC--

-CCGAGCGCCCATGTGGAAACC---CGTGTGTTCCGGTATCAGCTG
          -GGCTCGCGGGTACACCTTTGG---GCACACAAGGCCATAGTCGAC
          ||||||||||||||||||||
 extends←CCGAGCGCCCATGTGGAAACC
                              5'
                        ↓
TGCCAGTATACCATGTTCTAGCTCTCGC---CGAAGGACCGCCCGAAGCGGATGG---CCGAGCGCCCATGTGGAAACC
ACGGTCATATGGTACAAGATCGAGAGCG---GCTTCCTGGCGGGCTTCGCCTACC---GGCTCGCGGGTACACCTTTGG Probe Detection:
                                   GCTTCCTGGCGGGCTTCGCCTACC
                                   ||||||||||||||||||||||||
TGCCAGTATACCATGTTCTAGCTCTCGC---CGAAGGACCGCCCGAAGCGGATGG---CCGAGCGCCCATGTGGAAACC
ACGGTCATATGGTACAAGATCGAGAGCG---GCTTCCTGGCGGGCTTCGCCTACC---GGCTCGCGGGTACACCTTTGG
```

First Stage:

```
5'
GCTGTGGAAGCGGTACG→ extends
||||||||||||||||
---CGACACCCTTCGCCATGC---TGCCAGTATACCATGTTCTAGCTCTCGC---
---GCTGTGGGAAGCGGTACG---ACGGTCATATGGTACAAGATCGAGAGCG---

-CGAAGGACCGCCCGAAGCGGATGG---CCGAGCGCCCATGTGGAAACC---CGTGTGTTCCGGTATCAGCTG---
-GCTTCCTGGCGGGCTTCGCCTACC---GGCTCGCGGGTACACCTTTGG---GCACACAAGGCCATAGTCGAC---
                                                    ||||||||||||||||
                                         extends ←CGTGTGTTCCGGTATCAGCTG
                                                                      5'

⇓

CGACACCCTTCGCCATGC---TGCCAGTATACCATGTTCTAGCTCTCGC---CGAAGGACCGCCCGAAGCGGATGG---
GCTGTGGGAAGCGGTACG---ACGGTCATATGGTACAAGATCGAGAGCG---GCTTCCTGGCGGGCTTCGCCTACC

-CCGAGCGCCCATGTGGAAACC---CGTGTGTTCCGGTATCAGCTG
-GGCTCGCGGGTACACCTTTGG---GCACACAAGGCCATAGTCGAC
```

FIG. 1A

Second Stage:

```
5'    ACGGTCATATGGTACAAGATCGAGAGCG→ extends
      |||||||||||||||||||||||||||||
CGACACCCTTCGCCATGC---TGCCAGTATACCATGTTCTAGCTCTCGC---CGAAGGACCGCCCGAAGCGGATGG---
GCTGTGGGAAGCGGTACG---ACGGTCATATGGTACAAGATCGAGAGCG---GCTTCCTGGCGGGCTTCGCCTACC---

-CCGAGCGCCCATGTGGAAACC----CGTGTGTTCCGGTATCAGCTG
   |||||||||||||||||||||     ||||||||||||||||||||
   -GGCTCGCGGGTACACCTTTG----GCACACAAGGCCATAGTCGAC extends←CCGAGCGCCCATGTGGAAACC
        |||||||||||||||||||||
        5
             ⇓

TGCCAGTATACCATGTTCTAGCTCTCGC---CGAAGGACCGCCCGAAGCGGATGG---CCGAGCGCCCATGTGGAAACC
|||||||||||||||||||||||||||    ||||||||||||||||||||||||   |||||||||||||||||||||
ACGGTCATATGGTACAAGATCGAGAGCG---GCTTCCTGGCGGGCTTCGCCTACC---GGCTCGCGGGTACACCTTTGG
```

FIG. 1B

Probe Detection:

```
                          GCTTCCTGGCGGGCTTCGCCTACC
                          ||||||||||||||||||||||||
TGCCAGTATACCATGTTCTAGCTCTCGC---CGAAGGACCGCCCGAAGCGGATGG---CCGAGCGCCCATGTGGAAACC
||||||||||||||||||||||||||||   |||||||||||||||||||||||   |||||||||||||||||||||
ACGGTCATATGGTACAAGATCGAGAGCG---GCTTCCTGGCGGGCTTCGCCTACC---GGCTCGCGGGTACACCTTTGG
```

METHODS OF DETECTING BOVINE HERPESVIRUS 1 (BHV-1) IN SEMEN BY NUCLEIC ACID AMPLIFICATION

FIELD OF THE INVENTION

The present invention relates to novel compositions and methods for detecting the presence of Bovine Herpesvirus 1, an important pathogen of cattle. More particularly, the invention is directed to an accurate and sensitive method for the diagnosis of Bovine Herpesvirus 1 (BHV-1) infection using BHV-1 specific oligonucleotides as primers to amplify a particular region of the genome of BHV-1 which may be present in a clinical specimen. BHV-1 specific oligonucleotides may be used in the subsequent detection of the amplified regions of DNA.

BACKGROUND OF THE INVENTION

Bovine Herpesvirus 1 (BHV-1) is a significant pathogen of cattle. Infection with BHV-1 in cattle has also been termed "Infectious Bovine Rhinotracheitis" (IBR); "Infectious Pustular Vulvovaginitis" (IPV); and "Infectious Balanoposthitis" (IBP) (Pastoret et al., 1984, p.211–228 In: *Latent herpes virus infections in veterinary medicine*, (eds. Wittman, Gaskell, and Rizha), Martinus Nijhoff Publishers; and Straub et al., 1990, In: *Virus infections in ruminants*, (eds. Dinter and Morein), Elsevier Publishers). BHV-1 can cause abortions and respiratory, genital, and central nervous system diseases. Apparently, the mode of transmission is the cause of the various disease states, rather than variations in the virus serotype. BHV-1 is highly contagious and high titers of the virus can be excreted from the portal of entry, i.e. the virus can be found in saliva, nasal secretions, ocular discharges, genitourinary discharges, and semen of infected animals, depending on the various disease state. Of particular clinical and economic importance, bovine semen is capable of transmitting the disease to both cows and fetuses. The risk of transmission by semen is increased through the use of artificial insemination, where a single virus laden ejaculate may be diluted and inseminated in many susceptible cows (Drew et al., 1987, *Vet. Rec.* 121:547–548). It is important to note that the virus can survive in semen storage containers below −65° C., where it may also contaminate virus-free semen. Transmission of the viral agent can occur from an animal showing overt symptoms of disease, as well as during a subclinical infection where the appearance of disease or lesions is absent.

Once an animal is infected, and despite the infected animal mounting an adequate immune response, the virus may remain latent in ganglia and may be re-excreted in the respiratory and/or genital tract. Clinical recurrence can follow from reactivation of the virus from the latent state when an animal is stressed or given corticosteroids. Treatment of the disease is palliative, however, various vaccine formulations are available for use. Whole virus vaccines have limited use since killed vaccines often do not induce an immune response sufficient for providing adequate protection; and live virus vaccines can cause latency, with the possibility of reactivation, and often subsequent undesirable sequelae. BHV-1 polypeptide vaccines are being developed, particularly using the BHV-1 glycoproteins, gI, gIII, and gIV. Purified BHV-1 glycoproteins appear not to be highly antigenic, as direct application of the purified proteins to nasal mucosa did not result in detectable antibody formation. However, using cholera toxin as an adjuvant, mucosal immunization resulted in the induction of antibodies, although the duration of immunity was not established (Israel et al., 1992, *Virology*, 188:256–264). Protection is disclosed using recombinant BHV-1 glycoproteins as immunogens, particularly in the presence of an adjuvant (Babiuk et al., U.S. Pat. No. 5,151,267 issued Sep. 29, 1992).

Diagnosis of BHV-1 infection in a herd is usually based on serum neutralization tests, but other diagnostic tests have been developed (for a review, see Straub et al., supra). Tests used to detect the presence of BHV-1 in semen include virus isolation techniques (Sheffy et al., 1973, Proc. 77th Annual Meeting of the U.S. Animal Health Assoc., 131–137; Darcel et al., 1977, Proc. 20th Annual Meeting Am. Assoc. Vet. lab. Diagnost., 209–214; Kahrs et al., 1977, Proc. 20th Annual Meeting Am. Assoc. Vet. Lab. Diagnost., 187–208), and the "Cornell Semen Test" (Schultz et al., 1982, Theriogenol. 17:115–123). The Cornell Semen Test is currently the most sensitive method for detecting viral infectious agents in bull semen. In this test, pooled semen samples are inoculated into susceptible calves or sheep which undergo subsequent serological testing. The method has several disadvantages in that it is not possible to recognize which specific sample(s) of the pool is contaminated; the costs of the animal isolation facilities are high; and seroconversion of the inoculated animals takes up to 3 weeks. Thus, the virus isolation techniques and serological testing are both labor and time intensive.

Recent advances in molecular biology have provided several means for enzymatically amplifying nucleic acid sequences. Currently the most commonly used method, PCR (polymerase chain reaction, Cetus Corporation) involves the use of Taq Polymerase, known sequences as primers, and heating cycles which separate the replicating deoxyribonucleic acid (DNA) strands in exponentially amplifying a gene of interest. Other amplification methods currently under development include LCR (ligase chain reaction, Barnay, F., 1991, *Proc. Natl. Acad. Sci. USA*, 88:189–193) which utilizes DNA ligase, and a probe consisting of two halves of a DNA segment that is complementary to the sequence of the DNA to be amplified; enzyme QB replicase (Gene-Trak Systems) and a ribonucleic acid (RNA) sequence template attached to a probe complementary to the DNA to be copied which is used to make a DNA template for exponential production of complementary RNA; and NASBA (nucleic acid sequence-based amplification, Cangene Corporation) which can be performed on RNA or DNA as the nucleic acid sequence to be amplified.

Nucleic acid probes that are capable of hybridization with specific gene sequences have been used successfully to detect specific pathogens in biological specimens at levels of sensitivity approaching $10^3$–$10^4$ organisms per specimen. PCR has been applied to the field of medical diagnostics and veterinary medicine. PCR-based detection systems for BHV-1 have recently been described by Vilcek (1993, *J. Virol. Methods* 41:245–248), and by Israel et al. (1992, *Virology* 188:256–264). Neither reference describes the application of a PCR-based assay for detecting BHV-1 in semen samples. Both of these assays describe visualization for the detection of the PCR products using agarose gel electrophoresis. The sensitivity of one of the assays is in the order of $10^3$ plaque forming units (PFU) per ml in spiked nasal secretions (Israel et al., supra).

Coupled with a method that increases the specificity of amplification of BHV-1 target DNA sequences, the nested set of primers of the present invention can increase the level of sensitivity in detecting BHV-1 in a clinical specimen. Use of these primers may allow direct detection without relying on prior culture, conventional serological testing, or agarose gel electrophoresis. The present invention is particularly suited for detecting the presence of BHV-1 in bull semen. By using the oligonucleotides of the present invention, BHV-1 can be detected at a level of $5\times10^3$ TCID$_{50}$ (50% tissue culture infectious dose) per 0.5 ml of semen, as compared to the current "gold standard" of $5\times10^3$ to $2.5\times10^4$ TCID$_{50}$ in the Cornell Semen Test.

SUMMARY AND OBJECTS OF THE INVENTION

The present invention is directed to oligonucleotides useful as primers and/or probes in the detection of BHV-1 in clinical specimens. Also, the present invention is directed to a method of detecting the presence of BHV-1 in a clinical specimen wherein the oligonucleotides of the present invention may be used to amplify target nucleic acid sequences of BHV-1 that may be contained within a clinical specimen, and/or detect the presence or absence of amplified target nucleic acid sequences of BHV-1. The oligonucleotides may be used to amplify and/or detect gene sequences corresponding to BHV-1 gIV.

One object of the present invention is to provide oligonucleotides which can be used as nested primers to amplify a portion of the gIV gene of BHV-1 genomic DNA.

Another object of the present invention is to provide oligonucleotides which can be used as probes in the detection of amplified sequences of the gIV gene of BHV-1.

A further object of the present invention is to provide an accurate and sensitive method for detecting the presence of BHV-1 that may be contained in clinical specimens, particularly semen, by using the oligonucleotides disclosed to amplify and detect specific gIV gene sequences of BHV-1.

BRIEF DESCRIPTION OF THE FIGURES

In the accompanying drawings.

DETAILED DESCRIPTION OF THE INVENTION

Figure 1A:
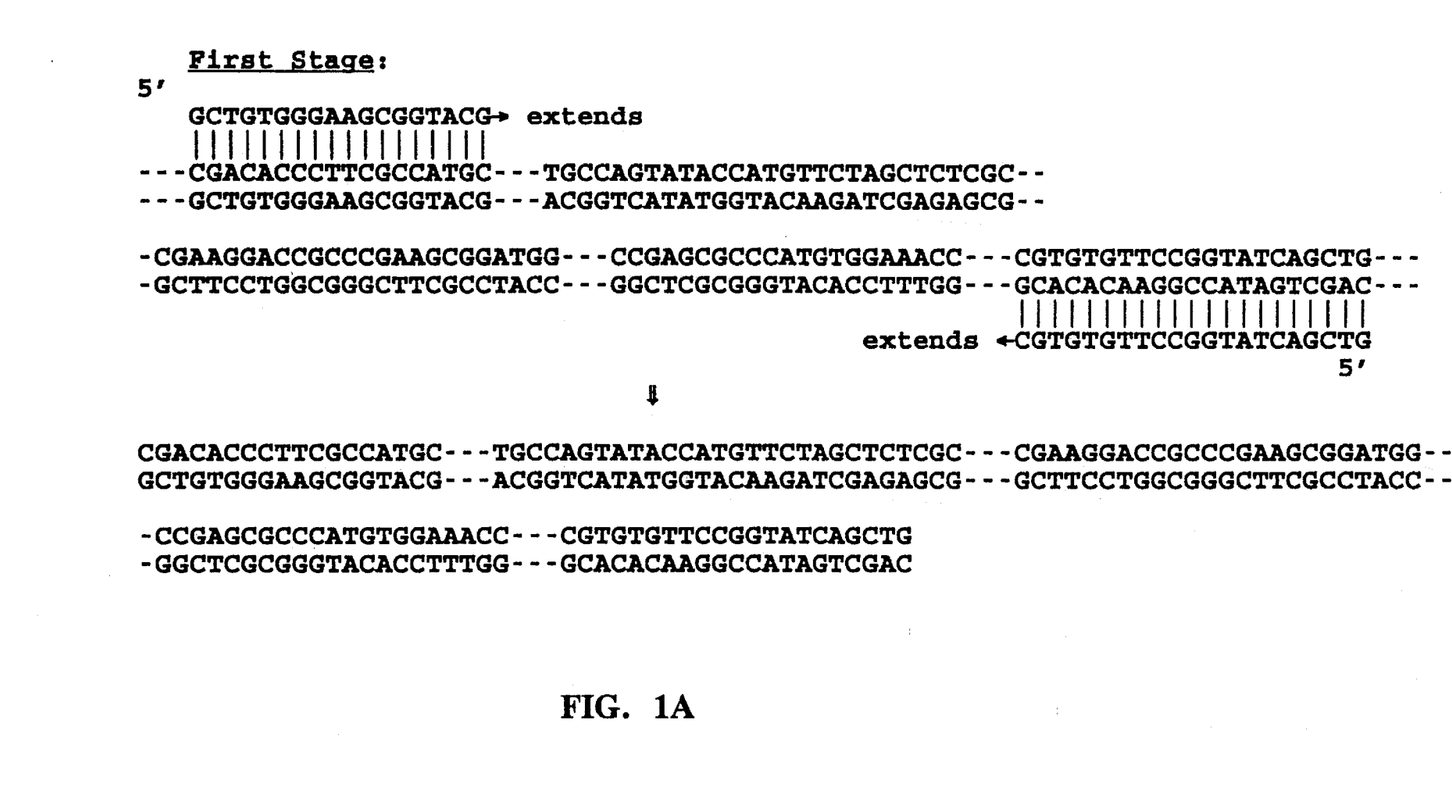
FIG. 1A is a schematic showing the first stage of nucleic amplification using the external primers of the present invention.
Figure 1B:
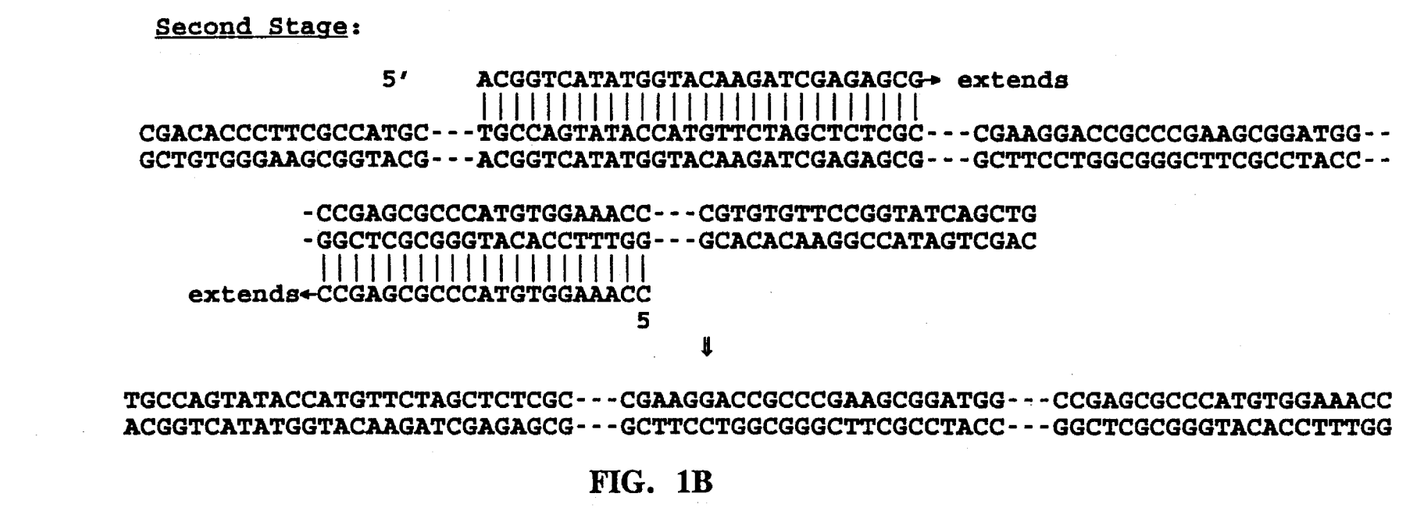
FIG. 1B is a schematic showing the second stage of nucleic acid amplification using the internal primers of the present invention.
Figure 1C:
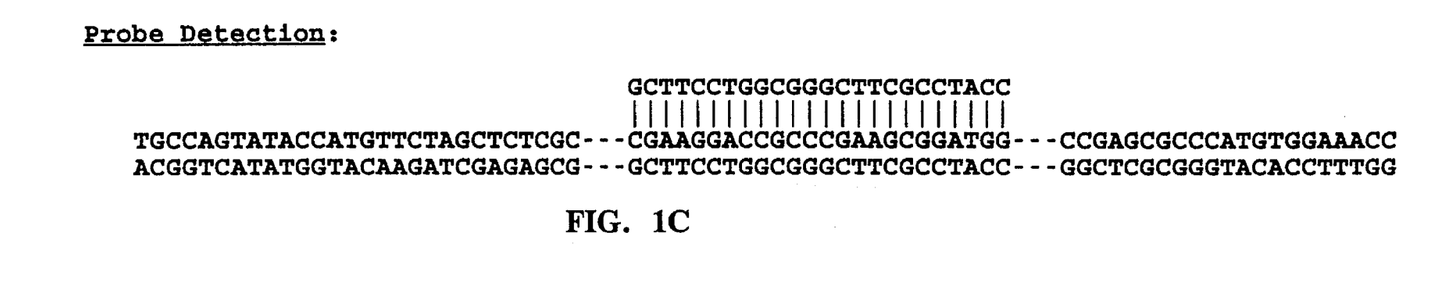
FIG. 1C is a schematic showing the detection of the amplified nucleic acid product from the second stage of amplification using the probe of the present invention.

The compositions and method of the present invention are directed to the detection of BHV-1 in a clinical specimen. The term "clinical specimen" is used herein to designate bovine bodily secretions, particularly bull semen. In one embodiment of the present invention, a set of nested oligonucleotide primers which are specific for BHV-1 gIV are used to hybridize to BHV-1 genomic DNA that may be present in DNA extracted from a clinical specimen. The oligonucleotide primers are selected so that there is a first set of two ("external") primers which are used in a nucleic acid amplification process to amplify a specific region of the gIV gene in BHV-1 viral DNA (FIG. 1A). A second set of two ("internal") primers are used in a second round of amplification to amplify an internal sequence of the amplified product from the previous round of amplification of the gIV gene sequence using the two outside primers (FIG. 1B). By amplification of BHV-1 DNA with a set of nested primers, the sensitivity and specificity of detection is increased. Background or nonspecific amplification is reduced due to the utilization of the binding of four primers; and because a smaller number of cycles may be used in each round of amplification. Because of the increase in specificity using this method, wherein the amplification process using the internal primers comprises a second layer of specificity, labeled dUTP may be incorporated directly into the amplified product. The molecule used to label dUTP may be selected from molecules used in the art to label nucleotides such as digoxigenin and biotin. Subsequent detection may then be achieved using a reverse dot blot with a capture oligonucleotide probe complementary to a sequence between the two internal nested primers (FIG. 1C).

Amplification of DNA may be accomplished by any one of the methods commercially available. For example, the polymerase chain reaction may be used to amplify the BHV-1 DNA. In each of the two stages of amplification, once the primers have hybridized to opposite strands of the target DNA, the temperature is raised to permit replication of the specific segment of DNA across the region between the two primers by a thermostable DNA polymerase. Then the reaction is thermocycled so that at each cycle the amount of DNA representing the sequences between the two primers is doubled and the specific amplification of the BHV-1 gIV DNA sequences, if present, results. Further identification of the amplified product, as being derived from BHV-1 DNA, may be accomplished by any one of several methods known in the art to detect amplified nucleic acid products (In the description of the invention, "amplified product", "amplified nucleic acid sequences" and "amplified nucleic acid molecules" are used interchangeably). One illustration of this embodiment uses a reverse dot blot assay to subsequently detect amplified products. This test utilizes one or more oligonucleotides as probes to "capture" by specific hybridization, and immobilize, amplified products derived from the gIV region of BHV-1. Thus, the oligonucleotides of the present invention have commercial applications in diagnostic kits for the detection of BHV-1 in secretions of infected cattle.

In another embodiment of the present invention, a method for the fast preparation of viral DNA from semen is used in conjunction with the oligonucleotides and method of the present invention for detecting BHV-1 in bovine semen.

In another embodiment of the present invention, the nested primers may be used to amplify and detect BHV-1 DNA from DNA extracted from a clinical specimen. In this embodiment, the internal primers used in the second stage of amplification may be labeled directly, or synthesized to incorporate label. Alternatively, since the second stage of amplification represents a second layer of specificity, labeled dNTPs may be added in the second stage so that multiple molecules of label are incorporated directly into the amplified product. Depending on the label used, the amplification products can then be detected, after binding onto an affinity matrix, using isotopic or colorimetric detection.

EXAMPLE 1

Viral Strains:

BHV-1 strain Colorado was grown for 24 hours in cultured MDBK cells previously shown to be free of mycoplasma and BVDV (Bovine Viral Diarrhea Virus) contamination. Following a single freeze-thaw cycle, the supernatant and cells were separated by low speed centrifugation and the supernatant was harvested. The $TCID_{50}$ of the supernatant was determined in MDBK cells using a standard microtiter methodology. Aliquots of the supernatant were stored at −80° C. until used for detection assays. Ten fold serial dilutions of the supernatant were then prepared in PBS just prior to use in the detection assays. Bovine Herpesvirus-3 (BHV-3) strain DN-99 was grown in culture in secondary bovine testes cells and the supernatant harvested as described above for BHV-1. This strain, together with the Movar type agents of cattle, has previously been designated as BHV-4. Both have recently been reclassified as BHV-3.

DNA Extraction:

While the following method for extracting viral DNA is particularly useful for the isolation of viral DNA from semen, a similar procedure may be used to extract viral DNA from other bovine secretions. Semen samples suspected of containing BHV-1 were centrifuged at 10,000×g to remove cells such as spermatazoa, and the supernatant harvested. An aliquot of the semen (either 3 µl, 6 µl, or 12 µl) was incubated at 56° C. for 30 minutes in 220 µl of a solution containing a weak cation exchange resin, 0.5 mg/ml proteinase K and 30 mM dithiothreitol (DTT). A desirable characteristic of the ion exchange resin for this procedure is that the ion exchanger have end groups, such as carboxylic acid, which have a high selectivity for binding metal ions that may catalyze the breakdown of DNA. Such a ion exchanger is CHELEX 100™ (Bio Rad Laboratories). Following the incubation, the mixture was centrifuged for 10 seconds. The tubes containing the mixture were then placed in a boiling waterbath for 8 minutes to heat inactivate the proteinase K, and the mixture was subsequently centrifuged for 3 minutes. A 10 µl aliquot of the supernatant was used in the amplification reaction. Previously described methods for the isolation of viral DNA from semen are time consuming and/or involve the use of hazardous chemicals and sophisticated equipment (Green et al., 1991, *Genitourin. Med.* 67:207–210; Mermin et al., 1991, *J. Infect. Dis.* 164:769–772).

Nucleic Acid Amplification Method:

An aliquot of the sample prepared from the DNA isolation method may be amplified using PCR. DNA to be amplified is placed in a reaction tube and mixed with 2.5 nmol each of dATP, dCTP, dGTP, dTTP, and labeled dUTP, 8% dimethylsulfoxide (DMSO), 2.5 pmol of the external primers, 25 pmol of the internal primers, 1.5 units of Taq polymerase in 1X PCR buffer (20 mM Tris-HCl pH 8.4, 50 mM KCl, 1.5 mM $MgCl_2$) with a total reaction volume of 25 µl. Note that both pairs of primers can be included in the same reaction mixture since the two pairs of primers have different melting temperatures ($T_M$). The external primers have a $T_M$ of around 63° C. while the internal primers have a $T_M$ of around 70° C. Therefore, the difference allows the annealing temperature after 10 cycles to be raised from 60° C. to 65° C. for the next 30 cycles, and allows primarily the internal primers to participate in the amplification in the later cycles. Thus, the amplifications were performed in a thermocycler with the amplification cycles consisting of an initial denaturation of 4 minutes at 92° C. followed by a first stage of amplification of 10 cycles of 1 minute at 94° C., 1 minute at 60° C., and 1 minute at 72° C.; then followed by a second stage of amplification of 30 cycles of 1 minute at 94° C., 1 minute at 65° C., and 1 minute at 72° C. with a final extension step of 6 minutes at 72° C. Amplification reactions were performed using a "hot-start" procedure by withholding the addition of the polymerase from the reaction until the first denaturation step was completed (Erlich et al., 1991, *Science*, 252:1643–1650). Such a procedure greatly increases amplification specificity by reducing mispriming.

Primers for Nucleic Acid Amplification:

Primer sequences which specifically hybridize to sequences in the gIV gene of BHV-1, and which are used in DNA amplification, are listed in Table 1. The sequence of the BHV-1 gIV was disclosed previously (Tikoo et al., 1990, *J. Virol.* 64:5132–5142). The primers were designed with the following desirable characteristics in mind:

As mentioned above, the two pairs of primers have different $T_M$s, therefore both pairs of primers can be included in the same reaction mixture.

The primers were designed so that they would not hybridize to the pseudorabies virus gp50 gene, or the herpes simplex virus type 1 gD gene. A computer search in a gene database (Genbank) revealed that these two genes are the most related to the BHV-1 gIV gene in the herpesvirus group. Further, the primers were demonstrated to show no cross hybridization with the closely related BHV-3.

Optimal conditions for each pair of primers for the amplification of BHV-1 DNA was determined by varying the $MgCl_2$ concentration in the PCR buffer, and by adding DMSO to the reaction mixture. The sensitivity of the PCR assay was optimized using DMSO ranging in concentrations between 0 and 10% in the reaction mixture containing DNA from 50 to 5,000 $TCID_{50}$. A concentration of about 8% DMSO was determined to be optimal. Using concentrations of $MgCl_2$ of between 1.5 and 4.5 mM, a concentration of about 1.5 mM was determined to be optimal.

Probes for Amplified Nucleic Acid Sequence Detection:

An oligonucleotide probe which specifically hybridizes to a sequence in the gIV gene of BHV-1 is listed in Table 1. In one embodiment of the present invention, the probe is used in a reverse dot blot assay to subsequently detect amplified products, wherein a poly-dT tail is added to the probe to immobilize it to a matrix, and the probe then captures, by specific hybridization, amplified products derived from the gIV region of BHV-1. In this embodiment, the capture probe is not labeled, but the internal primers or the amplified nucleic acid product is synthesized to incorporate label to facilitate detection. Alternatively, the label molecule contained in the internal primers or amplified product can be used as the targets of immobilized affinity molecules with specificity for that first label, and a different label can be incorporated into the probe to facilitate detection by hybridization with the immobilized amplified product. Non-isotopic or isotopic labelling of the probe may be accomplished using methods known in the art for incorporating the respective non-isotopic or isotopic label.

TABLE 1

Oligonucleotides specific for sequences of the gIV gene of BHV-1

| Oligonucleotide Sequence | Length | Gene location |
| --- | --- | --- |
| External Primers: | | |
| GCTGTGGGAA GCGGTACG<br>SEQ ID NO: 1 | 18 nt* | nt 351–368 |
| GTCGACTATG GCCTTGTGTG C<br>SEQ ID NO: 2 | 21 nt | nt 817–796 |
| Internal Primers: | | |
| ACGGTCATAT GGTACAAGAT CGAGAGCG<br>SEQ ID NO: 3 | 28 nt | nt 394–422 |
| CCAAAGGTGT ACCCGCGAGC C<br>SEQ ID NO: 4 | 21 nt | nt 716–696 |
| Probe: | | |
| GCTTCCTGGCGG GCTTCGCCTA CC<br>SEQ ID NO: 5 | 24 nt | nt 518–541 |

*nt — nucleotide

Detection of Amplified Nucleic Acid Sequences:

Initially, in the development of the present invention, amplified products were analyzed by 2.5% agarose gel electrophoresis in TBE (89 mM Tris-borate, 2 mM EDTA, pH8.2) containing ethidium bromide. Fragments were visualized using UV illumination, and compared to known nucleotide length markers to determine the length of the amplified nucleic acid sequences.

Subsequently, detection of amplified products was achieved using a reverse dot blot format. The reverse dot blot format is based upon the use of a synthetic oligonucleotide as a capture probe. Poly-dT tailing of the probe is accomplished by mixing 100 pmols of the probe with 2.5 mM dTTP and 51U terminal deoxynucleotidyl transferase in a total volume of 100 μl using enzyme buffer provided by the manufacturer. After incubation for 2 hours at 37° C., the reaction was stopped by the addition of 10 mM EDTA, pH 8.0. Following phenol:chloroform:isoamyl alcohol (25:24:1) extraction, the capture probe was stored at −20° C. until just before use. The capture probe was affixed onto a hybridization membrane by first denaturing the probe for 10 minutes at 95° C., followed by chilling the probe on ice, and spotting the probe onto the hybridization membrane where it was allowed to air dry. After baking the spotted membrane at 80° C. for 30 minutes, the membrane was incubated for 1 hour at room temperature in prehybridization solution (5X SSC, 0.1% (w/v) N-Lauroylsarcosine, Na salt, 0.02%(w/v) SDS, 5%(w/v) blocking reagent, 50%(v/v) formamide) and allowed to air dry.

Labeled amplified product was denatured at 95° C. for 10 minutes and chilled on ice for another 10 minutes. A 3 μl aliquot was mixed with 2 μl prehybridization mix and the 5 μl was spotted on to the membrane containing the capture probe in adjacent membrane regions and left to hybridize until all liquid was absorbed (~5 minutes). The membrane was then washed twice, at room temperature, for 5 minutes each in 2X SSC, 0.1%(w/v) SDS; and twice at 68° C., for 15 minutes each in 0.1X SSC, 0.1%(w/v) SDS. Detection of the labeled amplified product is accomplished by methods known in the art for that particular label. For example, detection of capture probe-bound digoxigenin labeled amplified product was performed according to the GENIUS™ KIT instructions (Boehringer Mannheim) with the concentration of blocking reagent in buffer 2(buffer B) raised to 2%(w/v). Both colorimetric and chemiluminescent detections were performed on the same membrane starting with chemiluminescence. For chemiluminescent detection, LUMI-PHOS™530 (Boehringer Mannheim) was used. Incubation was for 30 minutes followed by exposure to X-ray film for 15 minutes or to POLAROID 612 film for 1 minute using CAMLIGHT™ (Camera Luminometer System, Analytical Luminescence Laboratory). The membrane was then rinsed in buffer 3(buffer C) and developed using nitroblue tetrazolium salt (NBT) and 5-bromo-4-chloro-3-indolyl phosphate (X-phosphate). The color reaction was stopped after 10 minutes using TE buffer.

The reverse dot blot format of the present invention has the following advantages. First, hybridization was performed by directly spotting a small aliquot of the labeled amplified product thus a)reducing the amount of target needed for detection as well as the volume of the hybridization solution; b)decreasing the duration of the assay as the hybridization takes about 5 minutes; and c)allowing hybridization of different capture probes to the same membrane thereby detecting different amplified products. Secondly, there is no need to separate labeled amplified product from unincorporated label since the latter is not retained on the membrane. Lastly, the format provides versatility, i.e. a) the chemiluminescence signal could be permanently recorded rapidly, and with high sensitivity, on a photographic film providing alternative methods for recording results; and b) alternative methods of affixing the capture probe may be used such as by UV fixation, or by covalent attachment mediated by a coupling reagent.

EXAMPLE 2

Detection of BHV-1 in Semen

This embodiment is in accordance with the procedures and methods described in Example 1. To illustrate the specificity and sensitivity of the oligonucleotides and methods of the present invention for the detection of BHV-1 in bovine semen, commercial samples of extended (in whole milk extender) and raw semen were spiked with serial dilutions of the culture supernatant containing BHV-1. Artificially inoculated semen is a good model for the situation found in naturally infected semen, since natural infection of the semen usually occurs during ejaculation which results in free virus in the seminal plasma (Kahrs et al., 1977, Proc. 20th Annual Meeting Am. Assoc. Vet. Lab. Diagnost., 187–208; Straub et al., 1991, *Comp. Immun. Microbiol.*

Figure 2:
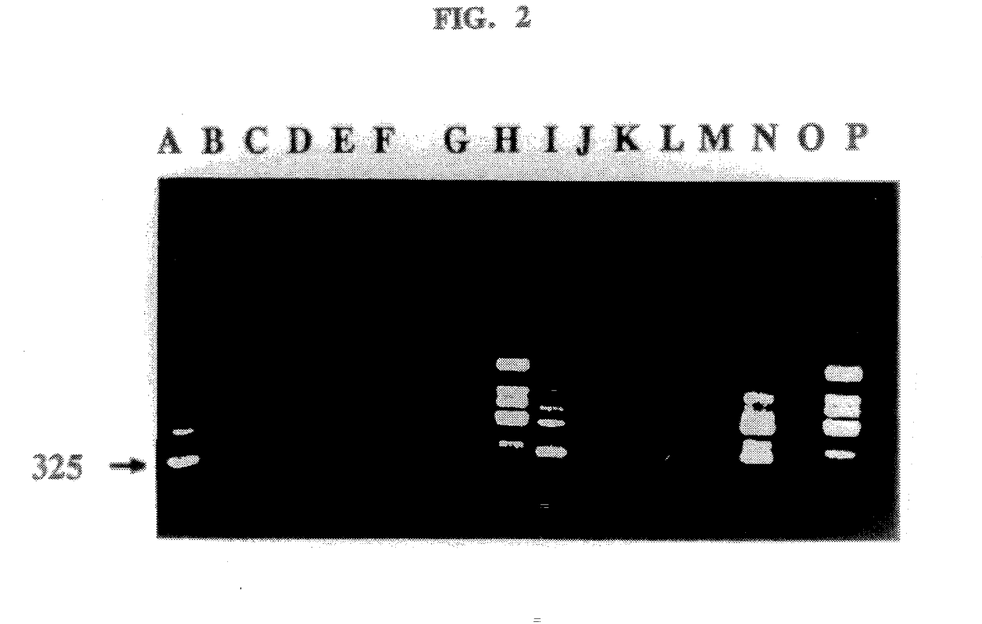
FIG. 2 represents an agarose gel corresponding to the amplification of BHV-1 DNA in raw semen (lanes A to G) and extended semen (lanes I to M). Lane H and P are marker fragments (in bp) of 1,353; 1,078; 872; 603; 310; 281; 234; 194; 118; 72. Quantities of BHV-1 particles (in TCID$_{50}$ per 0.5 ml semen) were: Lane A $5\times10^5$; Lane B $1\times10^5$; Lane C and I $5\times10^4$; Lane D and J $1\times10^4$; Lane E and K $5\times10^3$; Lane F and L $1\times10^3$; Lane G and M no virus added; Lane N 500 TCID$_{50}$ directly added to the amplification reaction; Lane O water directly added to the amplification reaction. The arrow marks the size of the amplified product expected from amplification with the internal primers.

*Infect. Dis.* 14: 175–186). DNA was extracted from the spiked samples and the resultant DNA was amplified by polymerase chain reaction using the nested primers specific for gIV gene sequences. Initially, the specificity and sensitivity was determined by subjecting the amplified products to agarose gel electrophoresis in the presence of ethidium bromide, and viewing the gel by UV transillumination. As shown in FIG. 2, lanes I to M, using extended semen there is a detectable amplified DNA product of 325 nucleotides, a size consistent with the expected fragment size from amplification with the internal primers. Also visible from the amplified product were two fragments of 600–800 base pairs (bp) which are consistently present, even from amplification using uninoculated extended semen as a control. Thus, the 600–800 bp fragments appear to be non-specific amplification products from spermatozoa present in the samples. This method was able to detect $1 \times 10^4$ TCID$_{50}$ BHV-1 per 0.5 ml extended semen. Since only the equivalent of approximately 0.5 µl semen was used in the PCR reaction, this corresponds to a sensitivity of about 10 TCID$_{50}$ per amplification reaction.

To investigate the effectiveness of the method of DNA preparation in accordance with the present invention for detecting BHV-1 in raw semen, DNA was extracted directly (without centrifugation) or with centrifugation to remove spermatozoa. Results using artificially inoculated raw semen, without centrifugation, showed that a maximum of 3 µl may be used in the ion-exchange step of DNA extraction with the subsequent use of 5 µl of the resultant DNA in an amplification reaction without experiencing inhibition in the amplification. As determined by agarose gel electrophoresis, the sensitivity of amplification using the nested primers was $1 \times 10^5$ TCID$_{50}$ BHV-1 per 0.5 ml raw semen without removal of spermatozoa by centrifugation in the DNA extraction procedure. The presence of spermatozoa in the amplification reaction gave rise to a significant amount of non-specific amplification products which may be seen on ethidium-bromide stained agarose gels as a smear in the sample lane.

Removing the spermatozoa from the raw semen by centrifugation prior to the DNA extraction allowed the use of 6 µl of the supernatant in the ion-exchange step, and 10 µl in amplification without experiencing detectable inhibition. When the spermatozoa are removed by centrifugation, the sensitivity of the assay was $5 \times 10^4$ TCID$_{50}$ BHV-1 per 0.5 ml raw semen as represented by a very faint band of 325 bp visible by agarose gel electrophoresis (FIG. 2, lane C).

EXAMPLE 3

Alternative Methods For Detection

Figure 3:
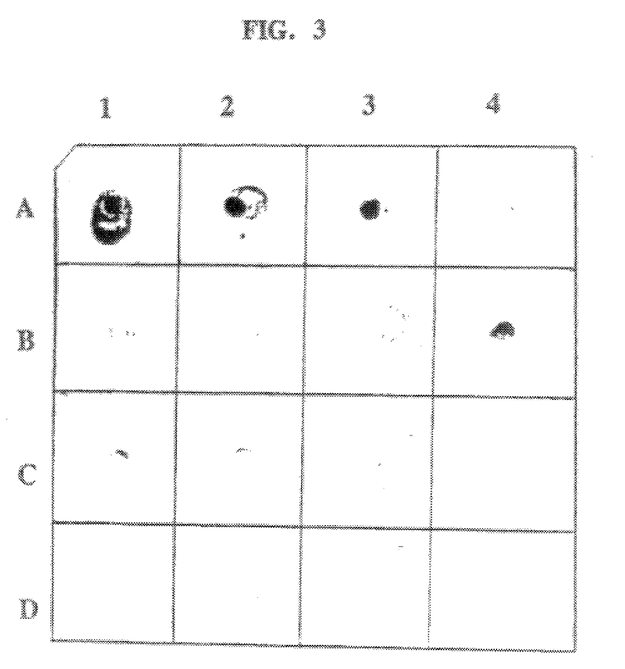
FIG. 3 represents a reverse dot blot showing the detection of BHV-1 in raw semen (squares A1 to B3) and extended semen (B4 to C4). Quantities of BHV-1 particles (in TCID$_{50}$ per 0.5 ml semen) were: A1 $5\times10^5$; A2 $1\times10^5$; A3 and B4 $5\times10^4$; A4 and C1 $1\times10^4$; B1 and C2 $5\times10^3$; B2 and C3 $1\times10^3$; B3 and C4 no virus added; D1 water directly added to the amplification reaction; D4 no amplified product spotted on filter.

Alternative methods known in the art may be used to improve the detection of amplified nucleic acid sequences in accordance with the compositions and methods of the present invention. The sensitivity of detection can be improved by subjecting the amplified products to a reverse dot blot assay. This embodiment is in accordance with the procedures and methods described in Examples 1 and 2. Detection by reverse dot blot was visualized colorimetrically by including digoxigenin-labeled dUTP in the nucleic acid amplification reaction so that the amplified product incorporated multiple molecules of label. The sensitivity of detecting BHV-1 in artificially inoculated extended semen was improved approximately two-fold when the amplified products were detected using the reverse dot blot assay. Therefore, the detection limit was lowered to $5 \times 10^3$ TCID$_{50}$ BHV-1 per 0.5 ml extended semen. FIG. 3, squares B4 to C4, illustrates the results using a reverse dot blot with nested primer amplification with artificially inoculated extended semen samples. A dark spot, representing the presence of amplified product derived from gIV sequences of BHV-1, is clearly visible for extended semen samples inoculated with $5 \times 10^3$ to $5 \times 10^4$ TCID$_{50}$ BHV-1 per 0.5 ml (FIG. 3, squares B4 to C2) while no background is detectable with the uninoculated extended semen (FIG. 3, square C4).

The sensitivity of detecting BHV-1 in artificially inoculated raw semen (with centrifugation to remove spermatozoa) was improved approximately ten-fold when the amplified products were detected using the reverse dot blot assay. Therefore, the detection limit was lowered to $5 \times 10^3$ TCID$_{50}$ BHV-1 per 0.5 ml raw semen (FIG. 3, square B). A high background was observed in reverse dot blot when DNA was prepared from semen without removing spermatozoa by centrifugation with subsequent amplification (data not shown).

Using this reverse dot blot format, and the primers and probe of the present invention, quantitation may be possible by end-point dilution, where the amount of virus is estimated by the last dilution to show a positive result.

Alternative methods of detection, which may be used with the compositions and methods of the present invention, are preferably those methods known in the art which use non-isotopic labeling and include a visual means of rapid detection. Such methods include: amplification with a labeled internal primer with dot blot and subsequent colorimetric detection; amplification with internal primers containing affinity tags (ex. biotin or digoxigenin; or one primer incorporating biotin and the other primer with a sequence specific for a DNA binding protein) followed by detection in an affinity-based assay (ex. ELISA); second stage amplification with internal primers containing fluorophores followed by fluorescence detection; and in second stage amplification, adding labeled dUTP (other than with digoxigenin, e.g. biotin, or fluorophore) to be incorporated into the amplified product. In each of these methods, it may be necessary to use the probe of the present invention to hybridize to the specific amplified product of 325 bp in distinguishing the specific amplified product vs. the nonspecific amplified products found in amplification of DNA extracted from semen.

One embodiment of non-isotopic detection involves incorporating biotin into the oligonucleotide primers of the present invention. The 5'-aminogroup of the primers may be biotinylated with sulfo-NHS-biotin, or biotin may be incorporated directly into the primer by synthesizing the primer in the presence of biotin-labeled dNTPs. The non-isotopic labeled primers are then used in amplifying DNA extracted from a clinical specimen as in accordance with the procedures and methods described in Example 1. Another embodiment involves adding biotin-dUTP to the amplification reaction, thereby incorporating the biotin label directly into the amplified product. In each of these embodiments, the detection for the presence or absence of amplified product derived from gIV sequences of BHV-1 may be accomplished by capturing the amplified product using hybridization to the probe of the present invention wherein the probe is immobilized/affixed to a matrix. Visualization may then be accomplished by a subsequent incubation with an avidin conjugate containing an enzyme which can be used to visualize the complex, followed by substrate development.

It should be understood that while the invention has been described in detail herein, the examples were for illustrative purposes only. Other modifications of the embodiments of the present invention that are obvious to those of ordinary skill in the art of molecular biology, medical diagnostics, and related disciplines are intended to be within the scope of the appended claims.

We claim:

1. A method for detecting the presence or absence of BHV-1 in semen, wherein the method comprises the steps of:

(a) centrifuging the semen to remove cells, and harvesting the supernatant;

(b) lysing BHV-1 particles, if present in the supernatant, and extracting nucleic acid molecules, by contacting and incubating the supernatant with an ion exchange resin and a protease;

(c) inactivating the protease, such as by heating the mixture from step (b);

(d) contacting the nucleic acid molecules, if present, with oligonucleotides SEQ ID No:1 and SEQ ID No:2 under suitable conditions permitting hybridization of oligonucleotides SEQ ID No:1 and SEQ ID No:2 to the nucleic acid molecules by first denaturing the nucleic acid molecules at a temperature of from about 85° C. to about 95° C., and then annealing oligonucleotides SEQ ID No:1 and SEQ ID No:2 to the denatured nucleic acid molecules at a temperature of from about 60° C. to about 63° C.;

(e) enzymatically amplifying a specific region of nucleic acid molecules comprising target sequences of BHV-1 in a first stage of nucleic acid amplification using oligonucleotides SEQ ID No:1 and SEQ ID No:2 as primers;

(f) contacting amplified nucleic acid molecules, if present from the first stage of nucleic acid amplification, with oligonucleotides SEQ ID No:3 and SEQ ID No:4 under suitable conditions permitting hybridization of oligonucleotides SEQ ID No:3 and SEQ ID No:4 to the amplified nucleic acid molecules by first denaturing the nucleic acid molecules at a temperature of from about 85° C. to about 95° C., and then annealing oligonucleotides SEQ ID No:3 and SEQ ID No:4 to the denatured nucleic acid molecules at a temperature of from about 65° C. to about 70° C.;

(g) enzymatically amplifying a specific region of amplified nucleic acid molecules, if present, in a second stage of nucleic acid amplification using oligonucleotides SEQ ID No:3 and SEQ ID No:4 as primers;

(h) contacting from the second stage of amplification amplified nucleic acid molecules present with oligonucleotide SEQ ID No:5 as a probe under suitable conditions permitting hybridization of complementary single-stranded molecules; and (i) detecting the presence of hybridized molecules so formed, whereby the presence of BHV-1 in the semen is detected with a sensitivity of at least $5 \times 10^3$ $TCID_{50}$ to $5 \times 10^4$ $TCID_{50}$ BHV-1 per 0.5 ml of semen.

2. The method of claim 1, wherein the detection is further facilitated by at least one of the oligonucleotides of step (e) having been labeled with a non-isotopic label selected from the group consisting of biotin, digoxigenin, and a fluorophore.

3. The method of claim 1, wherein the detection is further facilitated by including a labeled deoxynucleotide in the second stage of amplification according to step (g).

4. The method of claim 3, wherein the deoxynucleotide is dUTP and the label is selected from the group consisting of biotin and digoxigenin.

5. A method for the detection of BHV-1 in semen comprising separating, by centrifugation, cells including spermatozoa from a supernatant which contains BHV-1 particles that may be present; extracting nucleic acid molecules from the supernatant by incubating said supernatant in the presence of an ion exchange resin capable of binding to metal ions that catalyze the breakdown of DNA, and a protease; inactivating the protease and then using a set of nested oligonucleotide primers, specific for conserved sequences in the BHV-1 gIV gene, to hybridize to BHV-1 gIV sequences that may be present in the extracted nucleic acid molecules; wherein the oligonucleotide primers are selected so that there is a first set comprising two external primers which are used in a first stage of nucleic acid amplification, a second set comprising two internal primers which are used in a second stage of nucleic acid amplification to amplify an internal sequence of amplified nucleic acid molecules that may be present from the first stage of amplification; using an oligonucleotide as a probe to hybridize to BHV-1 specific sequences in amplified nucleic acid molecules that may be present from the second stage of amplification, and detecting the presence of hybridized molecules so formed whereby the presence of BHV-1 in semen is detected with a sensitivity of at least $5\times10^3$ TCID$_{50}$ to $5\times10^4$ TCID$_{50}$ BHV-1 per 0.5 ml of semen.

6. The method of claim 5, wherein the detection is further facilitated by at least one of the internal primers having been labeled with a non-isotopic label selected from the group consisting of biotin, digoxigenin, and a fluorophore.

7. The method of claim 5, wherein the detection is further facilitated by including a labeled deoxynucleotide in the second stage of amplification.

8. The method of claim 7, wherein the deoxynucleotide is dUTP and the label is selected from the group consisting of biotin and digoxigenin.

* * * * *

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 18 nucleotides
        ( B ) TYPE: nucleic acid
        ( C ) STRANDEDNESS: single- stranded
        ( D ) TOPOLOGY: linear     ( i i ) ORIGINAL SOURCE:
        ( A ) ORGANISM: Bovine Herpesvirus 1
        ( B ) STRAIN: Cooper     ( i i i ) FEATURE:
        ( A ) LOCATION: gIV gene region, 351- 368
        ( B ) IDENTIFICATION METHOD: by experiment
        ( C ) OTHER INFORMATION: hybridizes to Bovine Herpesvirus
                1 gene region     ( i v ) PUBLICATION INFORMATION:
        ( A ) AUTHORS: Tikoo, S.K.; Fitzpatrick, D.R.; Babiuk, L.A.;
            Zamb, T.J.
        ( B ) TITLE: Molecular Cloning, Sequencing and Expression of
            Functional Bovine Herpesvirus 1 Glycoprotein gIV
            in Transfected Bovine Cells
        ( C ) JOURNAL: Journal of Virology
        ( D ) VOLUME: 64
        ( E ) ISSUE: 10
        ( F ) PAGES: 5132-5142
        ( G ) DATE: October, 1990

( v ) SEQUENCE DESCRIPTION: SEQ ID NO: 1:

GCTGTGGGAA GCGGTACG                      18

( 2 ) INFORMATION FOR SEQ ID NO:2:

( i ) SEQUENCE CHARACTERISTICS:
        ( A ) LENGTH: 21 nucleotides
        ( B ) TYPE: nucleic acid
        ( C ) STRANDEDNESS: single- stranded
        ( D ) TOPOLOGY: linear     ( i i ) ORIGINAL SOURCE:
        ( A ) ORGANISM: Bovine Herpesvirus 1
        ( B ) STRAIN: Cooper     ( i i i ) FEATURE:
        ( A ) LOCATION: gIV gene region, 871- 796
        ( B ) IDENTIFICATION METHOD: by experiment
        ( C ) OTHER INFORMATION: hybridizes to Bovine Herpesvirus
                1 gene region     ( i v ) PUBLICATION INFORMATION:
        ( A ) AUTHORS: Tikoo, S.K.; Fitzpatrick, D.R.; Babiuk, L.A.;
            Zamb, T.J.
        ( B ) TITLE: Molecular Cloning, Sequencing and Expression of
            Functional Bovine Herpesvirus 1 Glycoprotein gIV
            in Transfected Bovine Cells
        ( C ) JOURNAL: Journal of Virology
        ( D ) VOLUME: 64
        ( E ) ISSUE: 10
        ( F ) PAGES: 5132-5142
        ( G ) DATE: October, 1990

( v ) SEQUENCE DESCRIPTION: SEQ ID NO: 2:

GTCGACTATG GCCTTGTGTG C                  21

( 2 ) INFORMATION FOR SEQ ID NO:3:

( i ) SEQUENCE CHARACTERISTICS:
        ( A ) LENGTH: 28 nucleotides
        ( B ) TYPE: nucleic acid
        ( C ) STRANDEDNESS: single- stranded
        ( D ) TOPOLOGY: linear     ( i i ) ORIGINAL SOURCE:
        ( A ) ORGANISM: Bovine Herpesvirus 1
        ( B ) STRAIN: Cooper     ( i i i ) FEATURE:
        ( A ) LOCATION: gIV gene region, 394- 422
        ( B ) IDENTIFICATION METHOD: by experiment
        ( C ) OTHER INFORMATION: hybridizes to Bovine Herpesvirus
                                        1 gene region     ( i v ) PUBLICATION INFORMATION:
        ( A ) AUTHORS: Tikoo, S.K.; Fitzpatrick, D.R.; Babiuk, L.A.;
                              Zamb, T.J.
        ( B ) TITLE: Molecular Cloning, Sequencing and Expression of
                        Functional Bovine Herpesvirus 1 Glycoprotein gIV
                        in Transfected Bovine Cells
        ( C ) JOURNAL: Journal of Virology
        ( D ) VOLUME: 64
        ( E ) ISSUE: 10
        ( F ) PAGES: 5132-5142
        ( G ) DATE: October, 1990

( v ) SEQUENCE DESCRIPTION: SEQ ID NO: 3:

A C G G T C A T A T    G G T A C A A G A T    C G A G A G C G                             2 8

( 2 ) INFORMATION FOR SEQ ID NO:4:

( i ) SEQUENCE CHARACTERISTICS:
        ( A ) LENGTH: 21 nucleotides
        ( B ) TYPE: nucleic acid
        ( C ) STRANDEDNESS: single- stranded
        ( D ) TOPOLOGY: linear     ( i i ) ORIGINAL SOURCE:
        ( A ) ORGANISM: Bovine Herpesvirus 1
        ( B ) STRAIN: Cooper     ( i i i ) FEATURE:
        ( A ) LOCATION: gIV gene region, 716- 696
        ( B ) IDENTIFICATION METHOD: by experiment
        ( C ) OTHER INFORMATION: hybridizes to Bovine Herpesvirus
                                        1 gene region     ( i v ) PUBLICATION INFORMATION:
        ( A ) AUTHORS: Tikoo, S.K.; Fitzpatrick, D.R.; Babiuk, L.A.;
                              Zamb, T.J.
        ( B ) TITLE: Molecular Cloning, Sequencing and Expression of
                        Functional Bovine Herpesvirus 1 Glycoprotein gIV
                        in Transfected Bovine Cells
        ( C ) JOURNAL: Journal of Virology
        ( D ) VOLUME: 64
        ( E ) ISSUE: 10
        ( F ) PAGES: 5132-5142
        ( G ) DATE: October, 1990

( v ) SEQUENCE DESCRIPTION: SEQ ID NO: 4:

C C A A A G G T G T    A C C C G C G A G C    C                                     2 1

( 2 ) INFORMATION FOR SEQ ID NO:5:

( i ) SEQUENCE CHARACTERISTICS:
        ( A ) LENGTH: 24 nucleotides
        ( B ) TYPE: nucleic acid
        ( C ) STRANDEDNESS: single- stranded
        ( D ) TOPOLOGY: linear (ii) ORIGINAL SOURCE:
  (A) ORGANISM: Bovine Herpesvirus 1
  (B) STRAIN: Cooper (iii) FEATURE:
  (A) LOCATION: gIV gene region, 518- 541
  (B) IDENTIFICATION METHOD: by experiment
  (C) OTHER INFORMATION: hybridizes to Bovine Herpesvirus 1 gene region (iv) PUBLICATION INFORMATION:
  (A) AUTHORS: Tikoo, S.K.; Fitzpatrick, D.R.; Babiuk, L.A.; Zamb, T.J.
  (B) TITLE: Molecular Cloning, Sequencing and Expression of Functional Bovine Herpesvirus 1 Glycoprotein gIV in Transfected Bovine Cells
  (C) JOURNAL: Journal of Virology
  (D) VOLUME: 64
  (E) ISSUE: 10
  (F) PAGES: 5132-5142
  (G) DATE: October, 1990

(v) SEQUENCE DESCRIPTION: SEQ ID NO: 5:

GCTTCCTGGC GGGCTTCGCC TACC                                          24